(12) United States Patent
Aldrich

(10) Patent No.: US 6,585,635 B1
(45) Date of Patent: Jul. 1, 2003

(54) METHOD AND SYSTEM FOR PERICARDIAL MODIFICATION

(75) Inventor: William N. Aldrich, Los Altos, CA (US)

(73) Assignee: Core Medical, Inc., Sunnyvale, CA (US)

( * ) Notice: Subject to any disclaimer, the term of this patent is extended or adjusted under 35 U.S.C. 154(b) by 170 days.

(21) Appl. No.: 09/715,866

(22) Filed: Nov. 16, 2000

Related U.S. Application Data

(60) Provisional application No. 60/154,430, filed on Sep. 17, 1999.

(51) Int. Cl.[7] .................................................. A61N 1/362
(52) U.S. Cl. ............................. 600/16; 600/17; 600/18
(58) Field of Search ............................. 600/16, 17, 18

(56) References Cited

U.S. PATENT DOCUMENTS

| | | | |
|---|---|---|---|
| 4,536,893 A | | 8/1985 | Parravicini |
| 5,131,905 A | | 7/1992 | Grooters |
| 5,222,980 A | * | 6/1993 | Gealow ........................ 623/3 |
| 5,273,518 A | | 12/1993 | Lee et al. |
| 5,385,528 A | | 1/1995 | Wilk |
| 5,533,958 A | | 7/1996 | Wilk |
| 5,603,337 A | | 2/1997 | Jarvik |
| 5,702,343 A | | 12/1997 | Alferness |
| 5,713,954 A | | 2/1998 | Rosenberg et al. |
| 5,785,705 A | | 7/1998 | Baker |
| 5,800,334 A | | 9/1998 | Wilk |
| 5,800,528 A | | 9/1998 | Lederman et al. |
| 5,910,124 A | * | 6/1999 | Rubin ........................ 601/153 |
| 6,059,750 A | * | 5/2000 | Fogarty et al. ........ 604/103.07 |
| 6,190,408 B1 | * | 2/2001 | Melvin ........................ 623/3.1 |
| 6,258,021 B1 | * | 7/2001 | Wilk ............................ 600/16 |
| 6,503,265 B1 | * | 1/2003 | Fogarty et al. ............. 606/192 |

* cited by examiner

Primary Examiner—Hieu T. Vo
Assistant Examiner—Johnny H. Hoang
(74) Attorney, Agent, or Firm—Orrick, Herrington & Sutcliffe LLP; James W. Geriak

(57) ABSTRACT

The invention adapts the pericardium for use as a pump bladder having a pump cavity formed by at least a portion of the pericardial space between the parietal pericardium and the visceral pericardium. The pump bladder is inflated to provide a compressive pressure on the heart and deflated to relieve the pressure. The pericardium is modified under conditions to improve the pumping characteristics of the pericardium as a pump bladder. A portion of the parietal pericardium may be attached to a portion of the visceral pericardium to isolate a portion of the pericardial space to form the pump cavity. The pericardium may be treated by stiffening, strengthening, tightening, shrinking, reshaping, or reducing the compliance or elasticity of the pericardium, or any combination thereof. The treatment may be carried out by heating the pericardium, applying a chemical to the pericardium, plicating the pericardium, or any combination thereof.

40 Claims, 4 Drawing Sheets

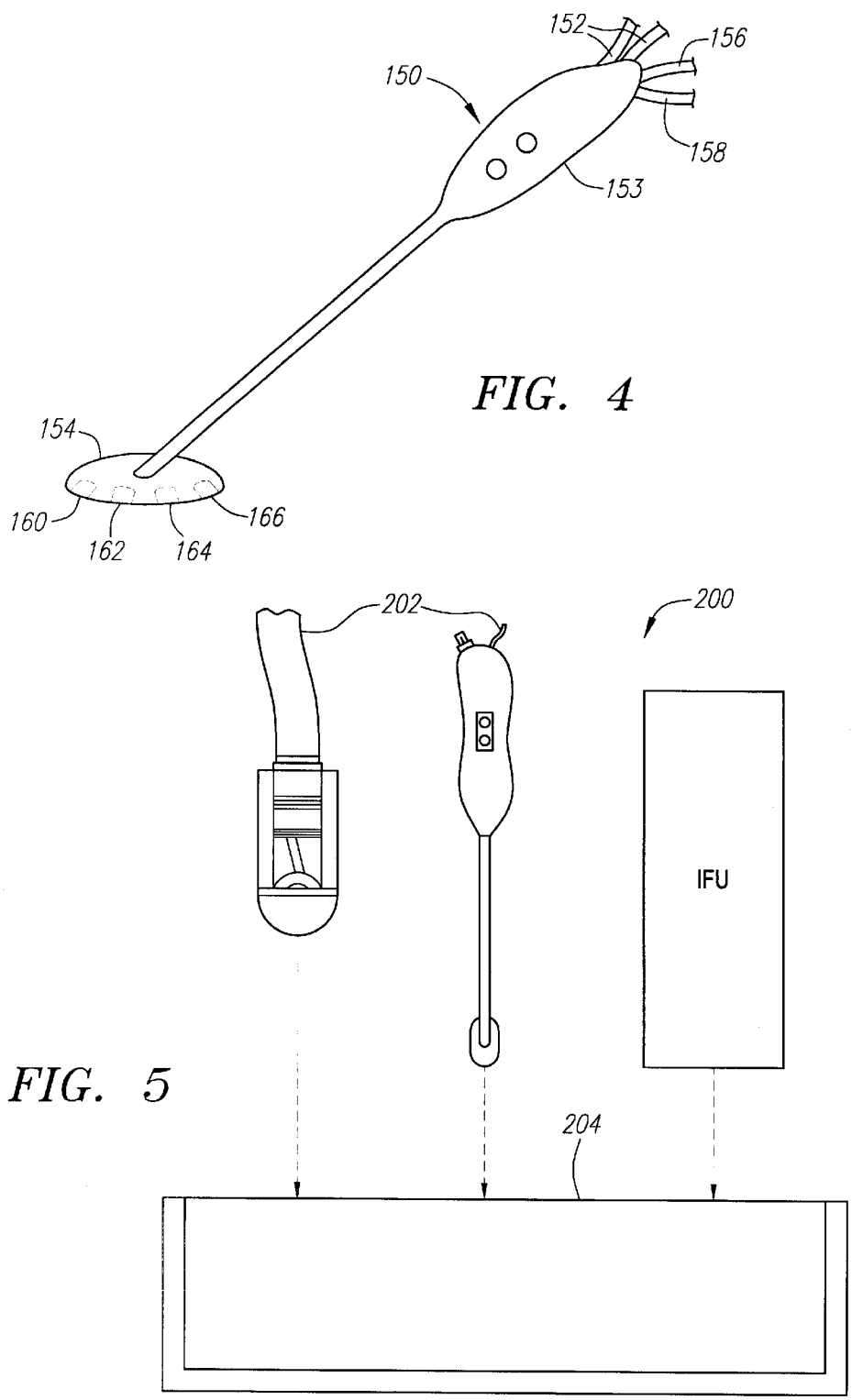

METHOD AND SYSTEM FOR PERICARDIAL MODIFICATION

CROSS-REFERENCES TO RELATED APPLICATIONS

This application claims benefit of U.S. Provisional Patent Application entitled "Method and System for Pericardial Enhancement," Serial No. 60/154,430, filed on Sep. 17, 1999, the disclosure of which is expressly incorporated herein by reference in its entirety.

BACKGROUND OF THE INVENTION

The present invention relates generally to pericardial modification, and more particularly to methods and systems for modifying the pericardium to adapt it for use as a pump bladder and to improve the pumping characteristics of the pericardium as a pump bladder.

A human heart includes a pair of valved muscular pumps. The right heart includes a right atrium and a right ventricle; the left heart includes a left atrium and a left ventricle. When the heart is in diastole, the left and right atria contract, forcing blood collected therein to flow to the expanding left and right ventricles, respectively. The blood collected in the ventricles is discharged in systole by contracting the muscles in the walls of the ventricles. The valves are closed between the left atrium and the left ventricle and between the right atrium and the left ventricle to prevent blood flow back to the atria. The wall muscles of the atria are relaxed to receive blood while the ventricles contract to discharge blood. At the end of systole, the wall muscles of the ventricles are relaxed, the valves between the atria and the ventricles are opened, and the wall muscles of the atria are contracted to flow blood into the ventricles, returning the heart to diastole. Some forms of heart failure are characterized by the inability of the heart to function effectively as a pump for the patient. Congestive heart failure generally refers to a condition where cardiac output has become so low that the body's circulatory requirements are not met.

Cardiac assist devices have been proposed for assisting heart performance. For instance, U.S. Pat. Nos. 5,707,336 and 5,910,124 disclose a ventricular assist device including an inflatable bladder that can be placed in contact with the heart to compress the left ventricle. U.S. Pat. No. 5,713,954 discloses a ventricular assist device in the form of an artificial myocardium that is wrapped around the ventricles to mimic the contraction-relaxation characteristics of the natural myocardium. U.S. Pat. No. 5,273,518 discloses a cardiac cup and/or aortic balloon pump in a cardiac assist apparatus. U.S. Pat. No. 5,131,905 is directed to a shell placed around the base of the heart for augmenting cardiac contractions.

U.S. Pat. Nos. 5,385,528, 5,533,958, and 5,800,334 are directed to an intrapericardial assist device having an inflatable cuff placed around the heart. A. Bencini et al., "The 'Pneumomassage' of the Heart," Surgery, Vol. 39, No. 3 (March 1956) discloses the rhythmical insulation of gas into the pericardial cavity via a cannula inserted though a small hole in the pericardium to produce rhythmical compression of the heart in patients suffering cardiac arrest.

SUMMARY OF THE INVENTION

The present invention is generally directed to methods and systems for treating patients suffering from heart conditions characterized by the deterioration of the pumping capability of the heart. The invention modifies the pericardium to adapt it for use as a pump bladder and to improve its pumping characteristics as a pump bladder. In specific embodiments, the pericardium is partitioned to isolate a portion of the pericardial space surrounding one or more of the cardiac chambers as the pump cavity for providing cardiac assistance using the pumping system of the present invention. The pericardium may be treated by heat, chemicals, plication, and the like to cause stiffening, strengthening, tightening, reshaping, and/or shrinking of the pericardium to enhance the performance of the pericardium as a pump bladder. The present invention will find its greatest use in patients at risk of suffering "congestive" heart failure, where the heart still functions, but with a significantly reduced cardiac output. The present invention will generally not find use for the emergency resuscitation of patients suffering a sudden cardiac arrest, although it could be used on those patients after they have been resuscitated by other means and methods.

In accordance with an aspect of the present invention, a method for aiding the operation of the heart includes adapting the pericardium for use as a pump bladder having a pump cavity formed by at least a portion of the pericardial space between the parietal pericardium and the visceral pericardium. The pericardium is modified under conditions to improve the pumping characteristics of the pericardium as a pump bladder.

In some embodiments, a portion of the pericardial space is isolated to form the pump cavity by attaching a portion of the parietal pericardium to a portion of the visceral pericardium. The attachment may be made by plication or bonding with an adhesive. In a specific embodiment, the attachment occurs generally along the AV groove to form a pump cavity in the portion of the pericardial space below the AV groove. The portion of the pericardial space forming the pump cavity may be sealed.

Modifying the pericardium may include treating the pericardium by stiffening, strengthening, tightening, shrinking, reshaping, or reducing the compliance or elasticity of the pericardium, or any combination thereof. The pericardium may be treated by heating the pericardium, applying a chemical to the pericardium, plicating the pericardium, or any combination thereof.

Another aspect of the invention is directed to a method for assisting the operation of the heart in a patient suffering from congestive heart failure using the pericardium adapted for use as a pump bladder having a pump cavity formed by at least a portion of the pericardial space between the parietal pericardium and the visceral pericardium, and modified to improve the pumping characteristics of the pericardium as a pump bladder. The method includes inflating the pump bladder to provide a compressive pressure on the heart, and deflating the pump bladder to relieve or reduce the compressive pressure on the heart.

In some embodiments, inflating the pump bladder includes pressurizing the pump bladder with a fluid, such as saline. In a specific embodiment, the fluid may include an antibiotic. A fluid flow line may be fluidicly coupled to the pump bladder, for instance, by forming an opening in the parietal pericardium and connecting a tubular graft through the opening to the pump cavity in the pericardial space. A pump may be connected with the fluid flow line for pumping the fluid to inflate and deflate the pump bladder. In a specific embodiment, the pump, fluid flow line, and pump bladder are connected in a way to form a closed circuit. The pump may be disposed externally or implanted in the body of the patient.

Optionally, the method may include monitoring the activity of the heart, for instance, by coupling a sensing electrode to the heart to obtain electrical signals from the heart. The inflating and deflating of the pump bladder may be controlled according to the sensed activity of the heart to assist contraction and facilitate expansion of the chambers of the heart.

In some embodiments, the signals of the heart sensed by the sensing electrode may be used to synchronize pumping action of the pump with the sensed activity of the heart.

Optionally, if the activity of the heart falls outside a preset acceptable range, the method may include pacing the heart by coupling a pacing electrode to the heart to generate a preselected rhythm. In specific embodiments, the inflating and deflating of the pump bladder are synchronized with the pacing of the heart.

BRIEF DESCRIPTION OF THE DRAWINGS

FIG. 4 is a perspective view of a device having radiofrequency electrodes for heating the pericardium and fluid flow ports for introducing a chemical for treating the pericardium; and FIG. 5 illustrates a kit constructed in accordance with the principles of the present invention.

DESCRIPTION OF THE SPECIFIC EMBODIMENTS

The present invention is directed to methods and systems for modifying the pericardium for use as a pump bladder and to improve its pumping characteristics as a pump bladder to treat patients suffering from heart conditions relating to the deterioration of the pumping capability of the heart.

Figure 1:
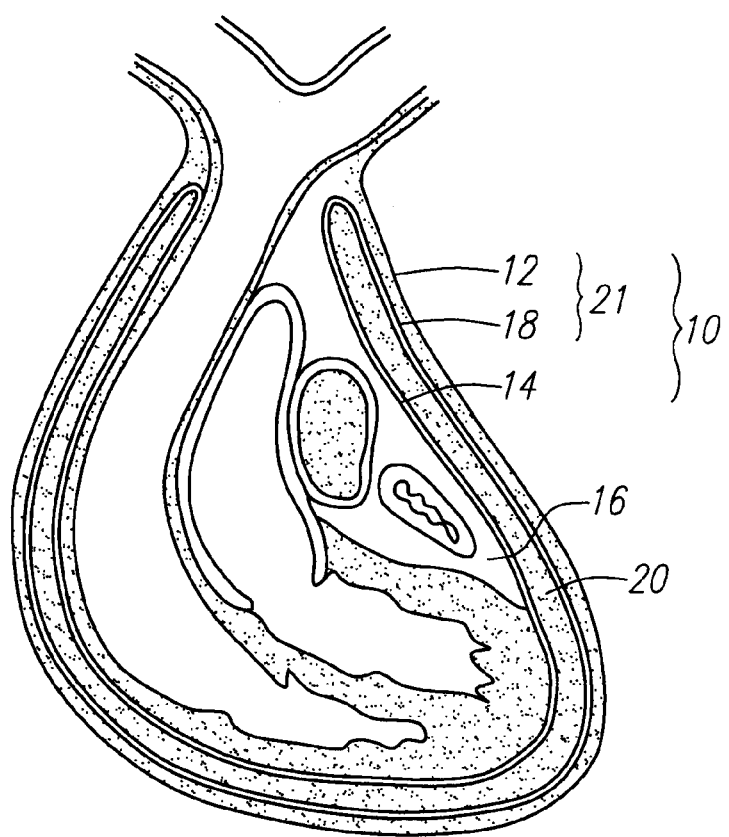
FIG. 1 is a schematic diagram of the heart.

The pericardium functions to prevent dilation of the chambers of the heart, lubricates the surfaces of the heart, and maintains the heart in a fixed geometric position. As shown in FIG. 1, the pericardium 10 includes the fibrous pericardium 12 and the serosal pericardium 14, 18. The fibrous pericardium 12 is a sac made of tough connective tissue, fully surrounding the heart without being attached to it. The serosal pericardium includes two sacs of serosal membrane, one inside the other. The inner (visceral) sac 14 adheres to the myocardium 16 and forms its outer covering known as the epicardium, while the outer (parietal) sac 18 lines the internal surface of the fibrous pericardium 12. The two serosal surfaces are separated by a film of fluid filling a space known as the pericardial space or pericardial cavity 20. The fibrous pericardium 12 and parietal sac 18 are sometimes referred to collectively as the pericardial sac 21.

The present invention relates to adapting the pericardium for use as a pump bladder and to modifying the pericardium to improve the pumping characteristics of the pericardium as a pump bladder. The pump cavity of the pump bladder is formed by at least a portion of the pericardial space between the parietal pericardium and the visceral pericardium.

Access to the pericardium to adapt it for use as a pump bladder may be made, for instance, through sternotomy, mini or partial sternotomy, thoracotomy, minithoracotomy, intercostal incision, or subxiphoid access channel. Access to the pericardium is also possible by a transvascular approach via the venous system, for example, through the right atrial appendage. The above methods of accessing the pericardium are known in the art, and other minimally invasive techniques may be employed as well.

Figure 2:
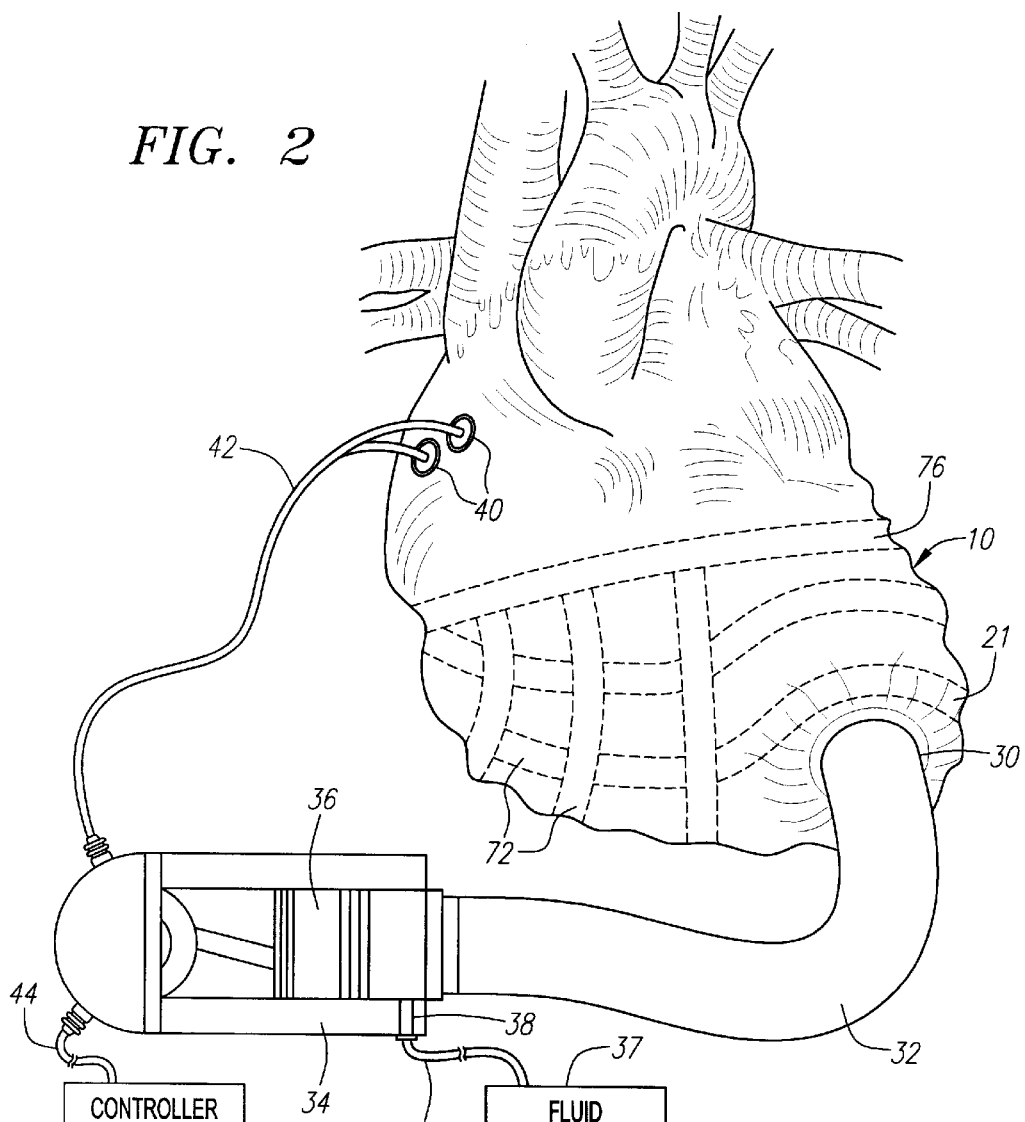
FIG. 2 is a perspective view of a pericardium adapted for use as a pump bladder illustrating an embodiment of the present invention.
Figure 2A:
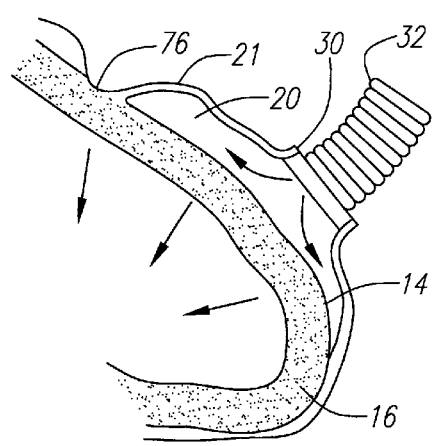
FIG. 2A shows a section of the pericardium of FIG. 2.

FIGS. 2 and 2A show a pericardium 10 adapted for use as a pump bladder having a pump cavity formed by a portion of the pericardial space 20. An opening 30 is made in the pericardial sac 21 to provide access to the pericardial space 20. A graft 32 is connected to the opening 30 and serves as a fluid flow line for transporting fluid between the pericardial space 20 and a pump 34.

The graft 32 is typically a tubular graft. The graft 32 may be made of a variety of bio-compatible materials, including, for example, Dacron™, Gortex™, bovine pericardium, and the like. The graft 32 desirably is substantially inelastic or noncompliant to avoid excessive expansion during inflation of the pump bladder, which may undermine the efficiency of the pumping action by limiting the maximum pressure and compression of the heart attainable in the pumping system.

The pump 34 may be a reciprocating or pulsating pump, and is configured to periodically pump fluid into and out of the pericardial space 20 to inflate and deflate the pump bladder. A variety of bio-compatible fluids may be used, including, for example, saline. Optionally, the fluid may include an antibiotic to protect against infection. The pump may be an external pump or an implantable pump that may be implanted in a patient's body.

An example of a suitable pump is a piston pump 34 having a moving piston 36, as shown in FIG. 2. In the embodiment shown, the pump 34, graft 32, and pericardial space 20 form a closed pumping system or circuit with the fluid enclosed therein. The piston 36 moves from a fully retracted position to a fully extended position and back in a full cycle. In the fully retracted position, the volume of the closed system expands to a maximum value and the pump bladder is deflated in that the pressure therein falls to a minimum level. In the fully extended position, the volume of the closed system contracts to a minimum value and the pump bladder is inflated in that the pressure therein rises to a maximum level. Inflation of the pump bladder provides a compressive pressure on the heart, while deflation of the pump bladder reduces or relieves the pressure.

The minimum pressure during deflation may be set at a level near, above, or below the atmospheric pressure. In some cases, it may be desirable to provide a minimum pressure that is as low as possible (e.g., in a near vacuum state), for instance, to assist the ventricles of the heart to expand to their maximum extent in diastole. In other cases, it may be sufficient to lower the pressure adequately to allow the ventricles to relax in diastole. During inflation, the maximum pressure level is desirably sufficiently high to assist the heart to achieve suitable contraction without reaching a level that may harm the heart.

In some embodiments, the extent of inflation and deflation of the pump bladder may be controlled and adjusted so as to provide a desired degree of assistance to cardiac contraction and expansion. This may be accomplished in a number of a different ways. For a closed pumping circuit, as shown in FIG. 2, one way to control the amount of inflation and deflation is by adjusting the amount of fluid in the system. To do so, the pump 34 may include a valve or port 38 that may be opened when desired to introduce additional fluid into or withdraw fluid from the closed pumping circuit via a fluid line 39 connected to a fluid source 37. The port 38 may also be used to bleed trapped air out of the pumping circuit. For an external pump, the valve 38 typically may be closed normally, and may be opened and coupled to the fluid line 39 for fluid transfer when desired. If the pump is implanted, the valve 38 typically may be an open port and the fluid line 39 may extend through an external port provided on the patient's body, which normally may be closed and may be opened when desired for fluid transfer.

It is understood that initially a process by trial and error may be used to adjust the amount of fluid in the closed pumping circuit until the desired pumping action is achieved. The valve 38 provides a convenient way to make the adjustment. After the pumping has reached steady state, additional adjustments may be made as desired (e.g., when conditions of the heart change).

Optionally, one or more sensing/pacing electrodes 40 may be coupled to the heart (e.g., the atrium), as shown in FIG. 2. The electrodes 40 may monitor the activity of the heart, for instance, by sensing electrocardiogram (EKG) signals of the heart. For example, the electrodes 40 may be used to monitor the heart rhythm. Upon detecting an abnormal or irregular rhythm, the electrodes 40 may be used to pace the heart. The electrodes 40 may also be used for defibrillation by delivering a defibrillating electrical shock to the heart when an abnormally fast rhythm is detected.

As shown in FIG. 2, a first lead 42 is connected between the electrodes 40 and the pump 34, and a second lead 44 is connected between the pump 34 and a controller 50. The controller 50 may include, for example, EKG processing circuitry and a power source, such as a battery. The controller 50 may receive and process the detected signals from the electrodes 40 via the leads 42, 44. Based upon the signals, the controller 50 may direct pump activation signals via the lead 44 to operate the pump 34. The activation signals may synchronize inflation of the pump bladder with contraction of the heart and deflation of the pump bladder with expansion of the heart, thereby enhancing the pumping action of the heart.

If the detected signal indicates that the activity of the heart falls outside an acceptable range (e.g., irregular or abnormal rhythm), the controller 50 may generate control signals to the electrodes 40 through the leads 44, 42 to pace and/or defibrillate the heart. The controller 50 may further generate pump activation signals in concert with the control signals to the electrodes 40. For example, the pump activation signals may synchronize the pumping action of the pump 34 with the heart rhythm produced by pacing signals to the heart.

It is understood that the monitoring and control system may be configured in other ways. For example, the lead 42 may connect the electrodes 40 to the controller 50 instead of the pump 34 in an alternate embodiment. Further, additional sensors may be provided for monitoring the activity of the heart and the operation of the pump 34.

The pump bladder formed by the pericardium 10 plays a vital role in the effective operation of the pumping system shown in FIGS. 2 and 2A. One way of modifying the pericardium to improve its pumping characteristics involves isolating a portion of the pericardial space 20 to form the pump cavity. Because the cardiac chambers expand and contract at different times, isolating the pump cavity to aid the pumping of particular chamber(s) may desirably provide more effective and efficient assistance to the heart's pumping performance. Moreover, partitioning the pericardial space to isolate a portion for use as a pump cavity may also reduce the volume of the pumping system, thereby resulting in a corresponding reduction in the size requirement for the graft 32 and pump 34.

By way of example, FIGS. 2 and 2A show a pump bladder formed by isolating the pericardial space 20 of the pericardium 10 below the AV (atrio-ventricular) groove 76 that separates the left and right atria from the left and right ventricles. This is done by attaching the parietal pericardium 18 to the visceral pericardium 14 along the AV groove 76. A variety of attaching methods may be used, including, for instance, bonding with bio-adhesives and plication. The connection is preferably sealed to prevent leakage of pumping fluid.

To bond the parietal pericardium 18 to the visceral pericardium 14, an adhesive may be applied, for instance, using an applicator inserted through the opening 30 of the pericardial sac 21. Examples of suitable adhesives include fibrin-based glues.

Plication may involve suturing, clipping, stapling and the like. Plication may be conveniently performed on the exterior of the pericardium 10, and typically involves plicating the pericardial sac 21 to the visceral sac 14 or to the myocardium 16.

By partitioning the pericardial space 20 to isolate the ventricles, the pump bladder may be deflated to facilitate expansion of the ventricles during diastole, and inflated to aid the contraction of the ventricles during systole. The embodiment shown in FIG. 2 is merely illustrative. Of course, the pericardial space may be partitioned to isolate a portion surrounding any one or more of the cardiac chambers for assistance using the pumping system of the present invention.

Another way to improve the pumping characteristics of the pericardium 10 is to treat the pericardium by stiffening, strengthening, tightening, shrinking, reshaping, or reducing the compliance or elasticity of the pericardium, or any combination thereof.

Strengthening the pericardium may enhance its ability to withstand high pressures as a pump bladder. Further, during inflation of the pump bladder, the piston 36 of the pump 34 may be moved to the fully extended position to reduce the volume of the closed pumping circuit in FIG. 2 to increase the pressure to compress the cardiac chambers. If the pericardium is too compliant or elastic, the pericardial sac 21 may expand excessively as a result of the increased pressure in the pericardial space 20, thereby limiting the increase in the internal pressure of the pump bladder. This undermines the performance of the pumping system by decreasing the effective compression of the heart. The efficiency of the pumping system may be improved by limiting the deformation of the pericardium by stiffening, tightening, reshaping, and/or reducing the compliance or elasticity of the pericardium. Furthermore, shrinking the pericardium decreases the volume of the pericardial space, resulting in a corresponding reduction in the size required for the graft 32 and pump 34, such that a more compact pumping system may be used.

One way to treat the pericardium to achieve improved pumping characteristics is to heat the pericardium. The collagen-containing tissue in the pericardium, in particular the fibrous pericardium, is modified when elevated in temperature. It is believed that the collagen fibers straighten when subjected to heat and, upon cooling, re-entwine or refold around each other, becoming shorter, tighter, thicker, or stronger, or some combination of the above. The heat treatment may improve the ability of the pericardium to serve as a pump bladder. Heating the pericardium may result in shrinking the pericardium and reducing the volume of the pericardial space as well.

Heat may be applied to or induced in the pericardium by a number of methods. One technique involves conductive heating by contacting the pericardium with a heating medium such as a heating element or a heated fluid. The pericardium may also be heated using radiant energy, for example, by placing a source of infrared radiation in close proximity to the tissue. Another technique heats the pericardium inductively by directing electromagnetic energy, such as radiofrequency, microwave, or light from either coherent or incoherent sources, into the tissue. Inductive heating may also be applied by passing an electric current through the tissue by means of electrodes inserted into or placed on the surface of the tissue. In addition, energy may be transmitted to the pericardium acoustically such as by ultrasound to induce heating of the tissue.

Some of these techniques, such as conductive heating, may require accessing the pericardium, while others, such as acoustic transmission of energy, may be performed noninvasively.

The pericardium may be treated from outside or from within the pericardial space. Treating the pericardium from the outside is less invasive because it does not require an incision of the fibrous pericardium and the parietal sac. The pericardial sac may remain closed with the possible exception of a small vent punctured through the pericardial sac for removing some or all of the pericardial fluid before, during, or after treating the pericardium. Treating the pericardium from the inside may be more desirable, however, since the inner surface is more homogenic than the outer surface, which is frequently covered in fat and small vessels. When treating the pericardium from the outside using energy or chemicals, the fat on the outer surface may desirably be removed for more effective treatment.

Fat removal may employ mechanical abrasion by scrapping or grinding with a scraper-like device or using a differential cutter that is biased to remove the fat in a manner similar to a Rotoblator™ device without harming the pericardium. The fat may also be removed by thermal ablation, chemically with a fat dissolving compound, or by suction. These techniques may be used individually or in combination.

Figure 3:
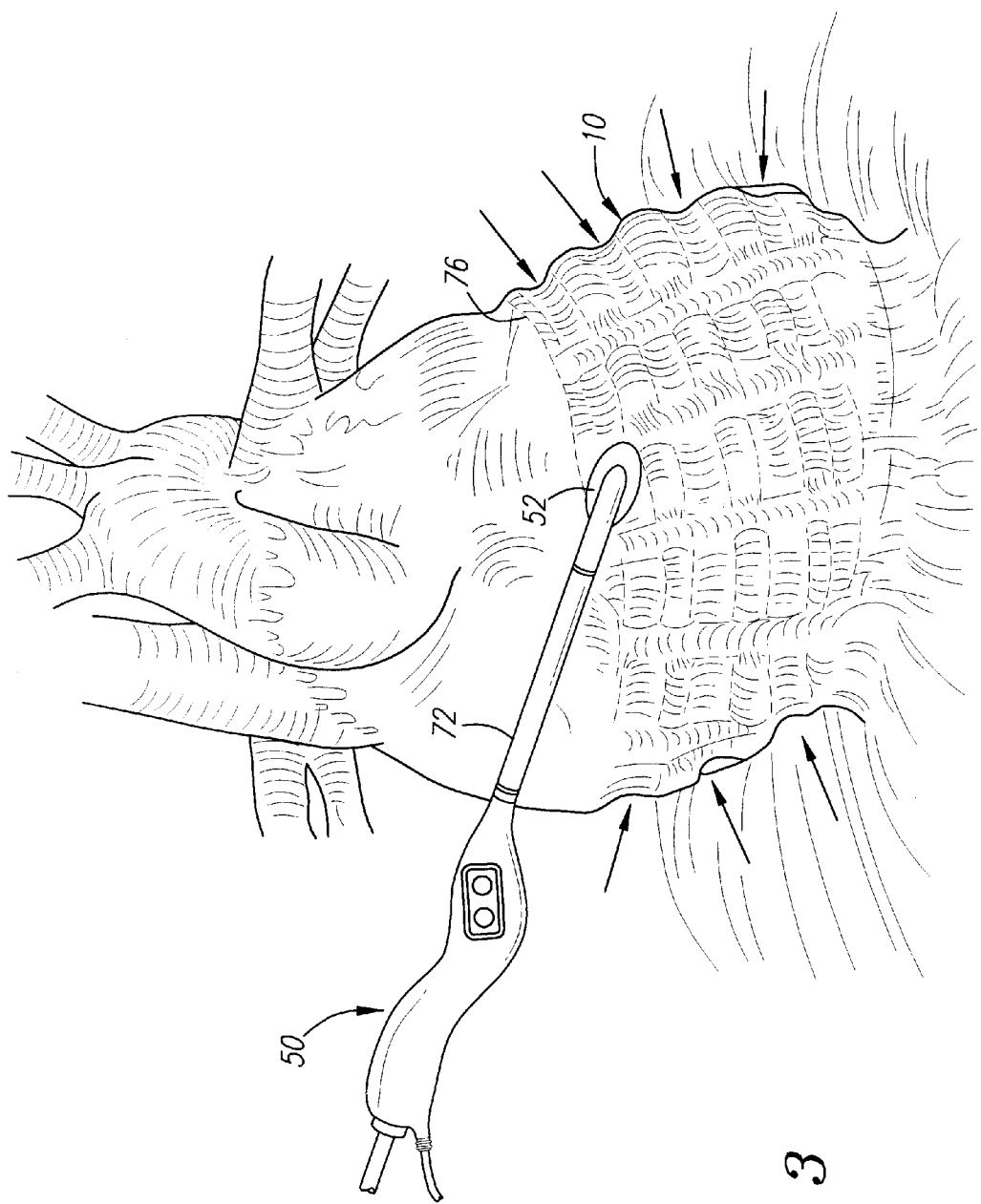
FIG. 3 is a perspective view of the pericardium illustrating treatment of the pericardium to improve its pumping characteristics.

FIG. 3 shows a heating device 50 having a distal heating portion 52 placed in contact with, or in close proximity to, the external surface of the pericardium 10. The heating portion 52 may be supported on a handpiece or probe 54. Alternatively, the heating portion 52 may be introduced into the patient's body minimally invasively using a catheter shaft. The catheter shaft is typically inserted through a guide wire lumen that guides the distal heating portion into the region of the heart adjacent the pericardium. Apparatus and techniques for negotiating a catheter through a patient, as well as internal exposure devices for presenting the target anatomy, are known in the art.

One preferred embodiment of the invention uses radiofrequency (RF) energy for heating. The distal portion 52 of the RF heating device 50 includes an RF electrode that is coupled to an RF generator provided outside of the patient's body. The RF heating device may employ a monopolar system in which the distal portion of the heating device includes a single active electrode, and a passive electrode is attached to the outer body surface of the patient. The patient's body serves to complete the electrical circuit. Alternatively, the RF heating device may apply RF energy in a bipolar manner by providing both active and passive electrodes on the distal portion. The active and passive electrodes are spaced apart from each other by a predetermined distance. The electrical circuit is completed by body tissue or fluid disposed between the active and passive electrodes.

The RF heating device delivers a controlled amount of RF energy so that there is an effective transfer of thermal energy to the target region of the pericardium to alter the collagen-containing connective tissue without causing dissociation or breakdown of the collagen fibers. One way to ensure viability of the pericardial tissue is to use a temperature-controlled RF heating device that senses the temperature during treatment and may be dynamically controlled to adjust the RF energy supplied to the electrode. Temperature-controlled RF heating devices are commercially available, for instance, from Oratec Intervention, Inc. of Menlo Park, Calif.

In FIG. 3, the heating device applies thermal energy along a plurality of bands of treated pericardium 72 that are spaced apart in a grid. Other treatment patterns may be used. Alternatively, the entire outer surface of the pericardium 10 may be subjected to heat treatment.

According to a specific embodiment, selective heating of the pericardium 10 takes place along the AV groove 76, which separates the left and right atria (LA, RA) from the ventricles, and extends down to the lower apex, as illustrated in FIGS. 2 and 3. This treats the portion of the pericardium adapted for use as the pump bladder. Optionally, the remaining portion of the pericardium may also be treated.

The above treatment techniques may be performed from inside of the pericardial space as well as from outside the pericardium. When the pericardium is treated from inside the pericardial space between the parietal sac and the epicardium, penetration of the fibrous pericardium and parietal sac is performed by any method known in the art. Prior to penetrating the pericardial sac, it is preferable to pull the sac away from the epicardium to avoid accidental damage to the epicardium. Access to the pericardial space may typically be done minimally invasively.

The heating device of FIG. 3 has a probe-like structure with a distal portion that is maneuvered around the pericardium to heat the tissue. Heating devices having other structures may be used, including, for example, heating baskets and umbrellas.

Instead of or in addition to heat, a chemical may be used to treat and enhance the pericardium. For instance, a chemical that causes stiffening or crosslinking of collagen fibers may be applied to the pericardium to cause stiffening, strengthening, tightening, reshaping, and/or shrinking of the pericardium to enhance the restraining and supporting capability of the pericardium around the heart. An example of a chemical that may be used is glutaraldehyde, which has been used to treat pericardial valves in valve replacement procedures. A nontoxic chemical is generally preferred so that it may be applied both to the external surface of the pericardium and from within the pericardial space.

FIG. 4 shows a device 150 for delivering RF energy and a chemical to treat the pericardium thermally and/or chemically. RF lines 152, such as wires or other conductors, extend between a proximal portion 153 and a distal portion 154 of the device 150. The RF lines 152 may be coupled to an RF generator (not shown) for supplying RF energy to the distal portion 154. The distal portion 154 includes an active electrode 160 and a passive electrode 162 coupled to the RF lines forming a bipolar system.

The device 150 also may include a chemical delivery line 156, connectable to a source of chemical, such as a pump (not shown), for introducing a chemical to the distal portion 154, and a vacuum line 158, connectable to a source of vacuum, for withdrawing the chemical. The distal portion 154 further includes a chemical inflow port 164 communicating with the delivery line 156 for introducing the chemical, and a vacuum port 166 communicating with the vacuum line 158 for removing the chemical from the treatment site. Contemporaneous removal the chemical as it is introduced may be particularly advantageous for chemicals that are toxic. Alternatively, instead of suction, removal of the chemical may be done using a sponge element and the like, which may be disposed on the distal portion 154.

Other ways of introducing the chemical to the pericardium may be used. For instance, a delivery tube may be guided into the pericardial space by a catheter for delivering the chemical into the space, and a vacuum tube may be placed at another location of the pericardium for removing the chemical.

Plication may also be used instead of or in addition to the above-described treatments to strengthen, shorten, tighten, reshape, and/or stiffen the pericardium. Plication of the pericardium typically involves plicating portions of the pericardial sac using plicating members to reduce the compliance and/or modify the shape of the pericardium. Suitable plication members include suture materials, clips, and the like.

The above procedures may be performed on a stopped heart or a beating heart. Moreover, treatment of the pericardium to improve its pumping characteristics may be performed before or after installation of the graft 32 and pump 34. Additional details of modifying the pericardium using heat, chemical, plication, and the like are described in U.S. Provisional Patent Application entitled "Method and System for Pericardial Enhancement," Serial No. 60/154,430, filed on Sep. 17, 1999, the disclosure of which is expressly incorporated herein by reference.

In FIG. 5, a kit 200 according to the present invention includes at least a member 202 for modifying the pericardium to adapt it for use as a pump bladder and to improve its pumping characteristics, and instructions for use (IFU) setting forth a method according to the present invention for modifying the pericardium. For illustrative purposes, the member 202 in FIG. 5 includes the graft and the pump of FIG. 2 and the heating device of FIG. 3. The member 202, however, may include any one or more of the devices described above, such as the devices shown in FIGS. 2–4. Optionally, the kit 200 may further include a device for accessing the pericardium., as well as packaging 204, typically in the form of a box, pouch, tray, tube, and the like. Instructions for use are usually printed on a separate sheet of paper in the form of a package insert, but may also be printed partly or wholly on the packaging itself.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

All patents, applications, and publications referred to above are incorporated herein by reference in their entirety.

What is claimed is:

1. A method for aiding operation of a heart, the method comprising:
   adapting the heart's pericardium for use as a pump bladder by forming a bladder from the pericardial tissue in at least a portion of the pericardium of the heart such that the cavity in said bladder comprises at least a portion of the pericardial space between the heart's parietal pericardium and visceral pericardium; and
   modifying the pericardium under conditions to improve the pumping characteristics of the pericardium as a pump bladder.

2. The method of claim 1, wherein the step of modifying the pericardium comprises isolating a portion of the pericardial space to form the pump cavity.

3. The method of claim 2, wherein the isolating step comprises attaching a portion of the parietal pericardium to a portion of the visceral pericardium to form the pump cavity in the pericardial space.

4. The method of claim 3, wherein the attaching step comprises plicating a portion of the parietal pericardium and a portion of the visceral pericardium.

5. The method of claim 3, wherein the attaching step comprises bonding a portion of the parietal pericardium and a portion of the visceral pericardium together with an adhesive.

6. The method of claim 3, wherein the parietal pericardium and the visceral pericardium are attached generally along the heart's AV groove to form a pump cavity in the portion of the pericardial space below the AV groove.

7. The method of claim 1, wherein the step of modifying the pericardium comprises treating the pericardium to reduce compliance of at least a portion of the pericardium forming the pumping bladder.

8. The method of claim 7, wherein the step of treating the pericardium comprises heating at least a portion of the pericardium forming the pumping bladder.

9. The method of claim 7, wherein the step of treating the pericardium comprises applying a chemical to at least a portion of the pericardium forming the pumping bladder.

10. The method of claim 7, wherein the step of treating the pericardium comprises plicating at least a portion of the pericardium forming the pumping bladder.

11. The method of claim 1, wherein the step of modifying the pericardium comprises treating the pericardium to shrink at least a portion of the pericardium forming the pumping bladder.

12. The method of claim 1, further comprising:
    inflating the pump bladder to provide a compressive pressure on the heart; and
    deflating the pump bladder to relieve or reduce the compressive pressure on the heart.

13. A method for assisting operation of a heart in a patient suffering from congestive heart failure using a pump bladder comprising the pericardial tissue of the heart, said bladder comprising a cavity formed by at least a portion of a pericardial space between the heart's parietal pericardium and visceral pericardium, and at least one of the parietal pericardium and the visceral pericardium being modified to improve the pumping characteristics of the pump bladder, the method comprising:
    inflating the pump bladder to provide a compressive pressure on the heart; and
    deflating the pump bladder to relieve or reduce the compressive pressure on the heart.

14. The method of claim 13, wherein the step of inflating the pump bladder comprises pressurizing the pump bladder with a fluid.

15. The method of claim 14, wherein the pressurizing step comprises coupling a fluid flow line to the pump bladder.

16. The method of claim 15, wherein the step of coupling the fluid flow line comprises forming an opening in the parietal pericardium and connecting a tubular graft through the opening in the parietal pericardium to the pump cavity in the pericardial space.

17. The method of claim 16, wherein the tubular graft includes a material selected from the group consisting of Dacron, Gortex, and bovine pericardium.

18. The method of claim 15, wherein the pressurizing step further comprises connecting a pump with the fluid flow line for pumping the fluid to inflate and deflate the pump bladder.

19. The method of claim 18, wherein the pump, the fluid flow line, and the pump bladder are connected in a closed circuit.

20. The method of claim 19, wherein the pump is implanted in the body of the patient.

21. The method of claim 13, further comprising:
    sensing activity of the heart; and
    controlling the inflating and deflating of the pump bladder according to the sensed activity of the heart to assist contraction and facilitate expansion of chambers in the heart.

22. The method of claim 21, wherein the sensing step comprises coupling a sensing electrode to the heart to obtain signals from the heart.

23. The method of claim 22, wherein the steps of inflating and deflating the pump bladder comprise coupling a pump with the pump bladder and operating the pump, and wherein controlling the inflating and deflating of the pump bladder comprises using the signals of the heart sensed by the sensing electrode to synchronize pumping action of the pump with the sensed activity of the heart.

24. The method of claim 13, further comprising pacing the heart.

25. The method of claim 24, further comprising synchronizing the inflating and deflating of the pump bladder with the pacing of the heart.

26. The method of claim 24, wherein the step of pacing the heart comprises coupling a pacing electrode to the heart to generate a preselected rhythm.

27. The method of claim 26, further comprising timing the inflating and deflating of the pump bladder to assist contraction and facilitate expansion of the chambers of the heart according to the preselected rhythm.

28. The method of claim 13, further comprising coupling an electrode to the heart to monitor activity of the heart.

29. The method of claim 28, wherein the pump bladder is inflated and deflated according to the activity of the heart if the activity of the heart falls within a preset acceptable range.

30. The method of claim 28, further comprising coupling a pacing device to the electrode to pace the heart if the activity of the heart falls outside a preset acceptable range.

31. A method for creating a pump bladder using a patient's heart, the method comprising:
    forming a pump bladder from the pericardial tissue of the heart which has a pump cavity comprising at least a portion of a pericardial space between the heart's parietal pericardium and visceral pericardium; and
    attaching a tubular graft to the heart, the tubular graft comprising a lumen communicating with the pump cavity for delivering fluid into the pump cavity.

32. The method of claim 31, wherein the forming step comprises isolating a portion of the pericardial space to form the pump cavity.

33. The method of claim 32, wherein the isolating step comprises attaching a portion of the parietal pericardium to a portion of the visceral pericardium to form the pump cavity in the pericardial space.

34. The method of claim 33, wherein the parietal pericardium and the visceral pericardium are attached generally along the heart's AV groove to form a pump cavity in the portion of the pericardial space below the AV groove.

35. The method of claim 31, further comprising modifying the pericardium under conditions to improve the pumping characteristics of the pericardium as a pump bladder.

36. A system for aiding operation of a heart, comprising:
    a pump;
    a tubular graft having a first end connected to the pump, and a second end configured for attachment to a pump bladder formed from the pericardial tissue of the heart;
    a sensor configured for detecting heart activity of the heart; and
    a controller coupled to the sensor and the pump, the controller configured for driving the pump in response to the heart activity detected by the sensor.

37. The system of claim 36, wherein the pump comprises a piston pump that is movable from a retracted position for deflating the pump bladder and an extended position for inflating the pump bladder.

38. The system of claim 36, wherein the sensor comprises an EKG electrode.

39. The system of claim 36, wherein the heart activity comprises contraction and expansion of the heart, and wherein the controller is configured for driving the pump to inflate the pump bladder with contraction of the heart and to deflate the pump bladder with expansion of the heart.

40. The system of claim 36, wherein the sensor comprises an electrode, and wherein the controller comprises a power source for delivering a defibrillation signal to the electrode when the detected heart activity is outside an acceptable range.

* * * * *